United States Patent [19]

Oediger et al.

[11] 4,370,280

[45] Jan. 25, 1983

[54] PHOSPHONOHYDROXYACETONITRILE, A PROCESS FOR ITS PREPARATION AND ITS USE AS AN INTERMEDIATE PRODUCT FOR THE PREPARATION OF MEDICAMENTS

[75] Inventors: Hermann Oediger, Cologne; Folker Lieb, Leverkusen; Hans Disselnkötter, Cologne, all of Fed. Rep. of Germany

[73] Assignee: Bayer Aktiengesellschaft, Leverkusen, Fed. Rep. of Germany

[21] Appl. No.: 308,734

[22] Filed: Oct. 5, 1981

[30] Foreign Application Priority Data

Oct. 23, 1980 [DE] Fed. Rep. of Germany ....... 3039997

[51] Int. Cl.$^3$ .................... C07C 120/00; C07C 121/36
[52] U.S. Cl. .......................... 260/465.6; 260/502.4 R; 424/212
[58] Field of Search ...................... 260/465.6, 465.5 R

[56] References Cited

PUBLICATIONS

C.A., 51, (1957), 3448h, Cherbuliez et al.
C.A., 51, (1957), 4312cd, Cherbuliez et al.
Morita et al., Bull. Chem. Soc. Japan, 51, 2169-2170 (1978).

*Primary Examiner*—Joseph Paul Brust
*Attorney, Agent, or Firm*—Sprung, Horn, Kramer & Woods

[57] ABSTRACT

The invention relates to phosphonohydroxyacetonitrile and a process for its production which comprises reacting phosphono formaldehyde, in salt form, with hydrocyanic acid (then, if desired, converting the free phosphonohydroxyacetonitrile to salt thereof. The phosphonohydroxyacetonitrile is useful, for example, as an intermediate for the production of phosphonohydroxyacetic acid, an antiviral agent.

5 Claims, No Drawings

PHOSPHONOHYDROXYACETONITRILE, A PROCESS FOR ITS PREPARATION AND ITS USE AS AN INTERMEDIATE PRODUCT FOR THE PREPARATION OF MEDICAMENTS

The invention relates to a certain new phosphorus compound and to an unobvious process for its production. The compound may be used as an intermediate product for the synthesis of pharmaceuticals.

According to the present invention there is provided the compound phosphonohydroxyacetonitrile of the formula

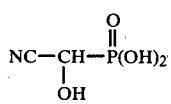
(I)

or a salt thereof.

The compound of the invention finds particular use in the synthesis of an antiviral agent in medicine.

According to the present invention there is further provided a process for the production of a compound of the invention, in which phosphonoformaldehyde of the formula

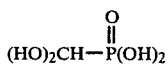
(II)

is reacted in the form of a salt thereof, with hydrocyanic acid, and the free phosphonohydroxyacetonitrile is converted, if desired, into a salt thereof.

The phosphonohydroxyacetonitrile according to the invention can be converted into salts by conventional methods.

Phosphonoformaldehyde is novel and is the subject matter of our copending patent application corresponding to German Patent Application No. P. 30 39 998.5 corresponding to U.S. Ser. No. 308,717 filed Oct. 5, 1981 and now allowed. It can be prepared by a process in which dialkoxymethanephosphonic acids [Bull. Chem. Soc. Japan 51 (1978), 2169] are warmed with water and, if appropriate, reacted with a base.

Preferred inorganic or organic salts of phosphonoformaldehyde which are starting substances for the process of the present invention are, for example, inorganic salts such as the alkali metal and alkaline earth metal salts, such as the sodium salt, and also organic salts such as the triethylammonium salt.

Anhydrous hydrocyanic acid or concentrated aqueous solutions of hydrocyanic acid are suitable as the hydrocyanic acid.

It is indeed in principle possible also to employ alkali metal salts of hydrocyanic acid, for example sodium cyanide, together with a bisulphite compound of the phosphonoformaldehyde. However, this process is less advantageous since the inorganic salts additionally formed, such as sodium sulphite, must be removed by additional separation operations.

Water is a possible diluent for the reaction according to the invention. However, if salts which are soluble in hydrocyanic acid are used, it is also possible to carry out the reaction without an additional diluent.

The process according to the invention is generally carried out in a temperature range from 0° C. to +40° C., preferably between +15° C. and +30° C.

In general, 1 mole of the compound (II) is reacted with 1 to 20 moles, preferably with 1.2 to 5 moles, of hydrocyanic acid. A larger excess of hydrocyanic acid does no damage, for example if the reaction is carried out in anhydrous hydrocyanic acid as the diluent.

The reaction time depends on the temperature and is generally between 15 minutes and 3 hours.

The resulting compound of formula (I) can be isolated by evaporation of the solution and, if appropriate, subsequent removal of salts on an acid ion exchanger.

Phosphonohydroxyacetonitrile is an intermediate product for the preparation of the antivirally active phosphonohydroxyacetic acid.

For example, phosphonohydroxyacetonitrile can be converted into the phosphonohydroxyacetic acid by hydrolysis of the nitrile group with hydrochloric acid.

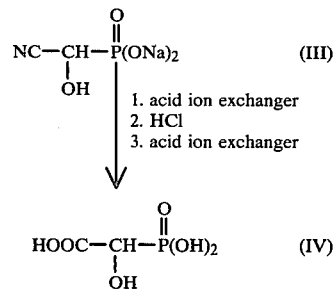

Phosphonohydroxyacetic acid has an action against herpes viruses in warm-blooded animals, in particular an action against Types I and II herpes simplex viruses.

The process for the production of phosphonohydroxyacetonitrile according to the present invention is illustrated by the following Example.

EXAMPLE

Na₂ salt of phosphonohydroxyacetonitrile 15 g (0.083 mole) of the dihydrate of the Na$_2$ salt of phosphonoformaldehyde were suspended in 30 ml of H$_2$O, and 10 ml of anhydrous hydrocyanic acid were then added at about +25° C. The temperature rose to +30° C.; a clear solution was formed. The mixture was kept at +30° C. for a further hour and the excess hydrocyanic acid and the water were then removed in vacuo and the residue was dried in vacuo. 15 g (95% of theory) of the dihydrate of the Na$_2$ salt of phosphonohydroxyacetonitrile were obtained in this manner.

$^1$H-NMR: δ=4.5 (1H, d, J=16.0 Hz) ppm (D$_2$O).
$^{13}$C-NMR: δ=122.3 (C≡N); 60.2 (d, J$_{C,P}$=133.3 Hz) ppm (D$_2$O).

The phosphonohydroxyacetonitrile thus obtained could be converted into phosphonohydroxyacetic acid in the following manner:

9.5 g (0.05 mole) of the dihydrate of the Na$_2$ salt of phosphonohydroxyacetonitrile were converted into phosphonohydroxyacetonitrile on an acid ion exchanger, the phosphonohydroxyacetonitrile was dissolved in 30 ml of concentrated hydrochloric acid and the solution was left to stand overnight. It was warmed for a further 4 hours to 85°–90° C., the solvent was removed in vacuo, the evaporation residue was taken up in water and the solution was filtered over an acid ion exchanger. The filtrate was evaporated in vacuo, the solution obtained by dilution with water was adjusted to a pH value of about 7.5 and the water was removed in vacuo. 8.3 g (75% of theory) of the Na$_3$ salt of phosphonohydroxyacetic acid were obtained in this manner.

$^1$H-NMR: $\delta = 4.1$ (1H, d, J = 18 Hz) ppm (D$_2$O).

$^{13}$C-NMR: $\delta = 168.1$ (COO$^{\ominus}$); 73.7 (d, $J_{C,P} = 134.1$ Hz) ppm (D$_2$O).

If desired, it was also possible to triturate the evaporated filtrate with ethyl acetate and to obtain the resulting solid phosphonohydroxyacetic acid by filtration and drying.

Yield: 5.1 g (70% of theory), melting point: 153°–154° C.

$^1$H-NMR: $\delta = 4.7$ (1H, d, J = 18 Hz) ppm (D$_2$O).

What is claimed is:

1. A compound which is phosphonohydroxyacetonitrile of the formula

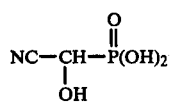

or a salt thereof.

2. A process for the production of the compound of the Formula (I) according to claim 1, which comprises reacting, in the temperature range from 0° C. to +40° C., phosphonoformaldehyde of the formula

in the form of a salt, with hydrocyanic acid, and isolating the resulting phosphonohydroxyacetonitrile.

3. A process according to claim 2, in which the sodium salt or triethylammonium salt of phosphonoformaldehyde is used.

4. A process according to claim 2, in which the reaction is carried out using water as the diluent.

5. A process according to claim 2, in which a salt of phosphonoformaldehyde which is soluble in hydrocyanic acid is used and the reaction is carried out without an additional diluent.

* * * * *